Figure 1:
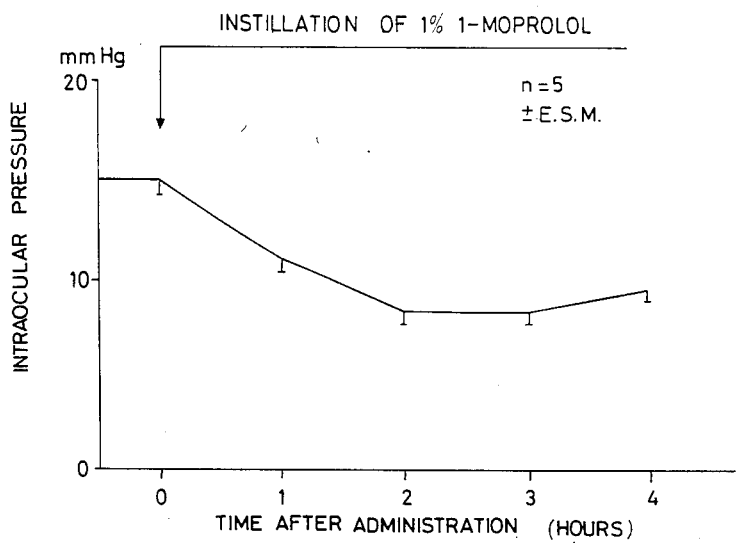

United States Patent [19]

Virno

[11] Patent Number: 4,647,590

[45] Date of Patent: Mar. 3, 1987

[54] PHARMACEUTICAL COMPOSITIONS AND THEIR USE IN THE TREATMENT OF GLAUCOMA

[75] Inventor: Michele Virno, Rome, Italy

[73] Assignee: SIMES, Societa Italiana Medicinali e Sintetici S.p.A., Milan, Italy

[21] Appl. No.: 580,239

[22] Filed: Feb. 15, 1984

[30] Foreign Application Priority Data

Feb. 15, 1983 [IT] Italy ................................ 19600 A/83

[51] Int. Cl.⁴ ............................................ A61K 31/135
[52] U.S. Cl. ...................................... 514/651; 514/913
[58] Field of Search ................. 424/330; 514/651, 913

[56] References Cited

U.S. PATENT DOCUMENTS

| | | | |
|---|---|---|---|
| 4,281,654 | 8/1981 | Shell et al. | 424/19 |
| 4,303,637 | 12/1981 | Shell et al. | 424/14 |
| 4,463,176 | 7/1984 | Dennis et al. | 544/128 |

*Primary Examiner*—Douglas W. Robinson
*Attorney, Agent, or Firm*—Cushman, Darby & Cushman

[57] ABSTRACT l-moprolol is instilled locally in the form of an opthalmic pharmaceutical composition to treat glaucoma.

11 Claims, 7 Drawing Figures

VASOMOTOR ACTIVITY OF 1-MOPROLOL ON CILIARY CIRCULATION EVALUATED THROUGH THE ALTERATION OF THE BLOOD/AQUEOUS HUMOUR BARRIER PERMEABILITY

PHARMACEUTICAL COMPOSITIONS AND THEIR USE IN THE TREATMENT OF GLAUCOMA

This invention relates to new pharmaceutical compositions and to their use in the treatment of glaucoma.

More particularly this invention relates to new pharmaceutical compositions containing 1-moprolol as active ingredient.

1-moprolol (LEVOTENSIN ®-Simes) is a drug useful in the therapy of arterial hypertension as well as in the treatment and in the prevention of coronary insufficiency.

Now it has been surprisingly found that 1-moproplol shows an intraocular hypotensive effect equivalent to that of Pilocarpine and Timolol without causing those side effects and inconveniences which are inherent to Pilocarpine (myosis) and to Timolol (bradychardia, local anesthesia and tachyphylaxis).

It is known that a drug is able to exhert an intraocular hypotensive effect when it is vasoactive at the level of ciliary body in reducing the production of aqueous humour.

In addition the drug must be well tolerated locally when instilled and it must be able to pass through the intraocular structure to reach the ciliary body. Furthermore, the vascular properties of the drug must be exerted at local level without causing any systemic effect.

Therefore, the most appropriate tests to evaluate the intraocular effects of a drug are the followings:

- effect of the drug administered locally on the normal intraocular pressure,
- evaluation of the entity and duration of the intraocular hypotensive effect of the drug on experimentally induced intraocular hypertension,
- local tolerability of the drug (biomicroscopy examination of the anterior segment, keratoesthesia, tear secretion: 15 days treatment; observation every 72 hours),
- possible cardiovascular effects after drug installation,
- involvement of the ocular circulation in the systemic vascular phenomenon induced by intravenous administration of the drug: examination of the effect on both the systemic arterial pressure and the intraocular pressure recorded constantly and simultaneously,
- vasomotor activity of the drug on the ciliary body: correlation among vascular activity, vascular permeability and production of aqueous humour,
- comparison of the intraocular hypotensive effect of the drug with respect to the most active anti-glaucoma agents (administered at least after 48 hours one from the other),
- evaluation of the local anesthetic effect "in vitro" on the eye of a cat isolated together with a substantial portion of the optical nerve and with the ciliary nerves up to the ciliary ganglion. The system is plunged into a Krebs solution and a ciliary nerve branch connected with a recorder. The cornea is submitted to light mechanical percussions and the responses of the ciliary nerve recorded either when the system is plunged into a Krebs solution or into a medicated solution,
- tachyphylaxis evaluation by administering the drug twice a day for a 30 day period in experimentally induced ocular hypertension and measuring the ocular pressure every two days at different hours.

In these tests 1-moprolol has shown a remarkable hypotonic effect without showing any appreciable local or systemic side effect.

The pharmaceutical preparations useful to the purpose are those commonly used in the ophthalmic field such as, for example, collyria or ointments.

These preparations contain a suitable amount of 1-moprolol or of a pharmaceutically acceptable acid addition salt thereof together with diluents, preservatives, buffers, stabilizers etc. commonly used by the artisan. In addition, they may be ready for the use or prepared extemporaneously.

Preferably these preparations contain a quantity of 1-moprolol ranging from 0.1 to 20%; still more preferred forms are those containing from 1 to 8% of 1-moprolol.

Examples of suitable pharmaceutical forms are

1. Powder:
   (a)
   1-moprolol: 0.100 g
   sodium chloride: 0.060 g
   (b)
   1-moprolol: 0.200 g
   sodium chloride: 0.030 g each of the above powders is taken up, at the time of use, with the following Solvent: benzalkonium chloride 0.001 g—disodium EDTA 0.001 g—disodium phosphate 12H$_2$O 0.0243 g—monosodium phosphate H$_2$O 0.0074 g—distilled water q.s. to 10 ml.

Figure 2:
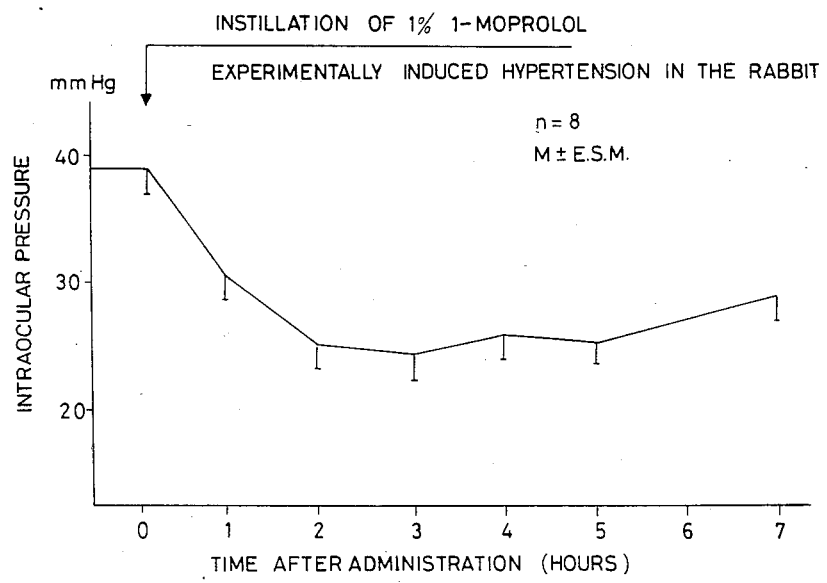
Figure 3:
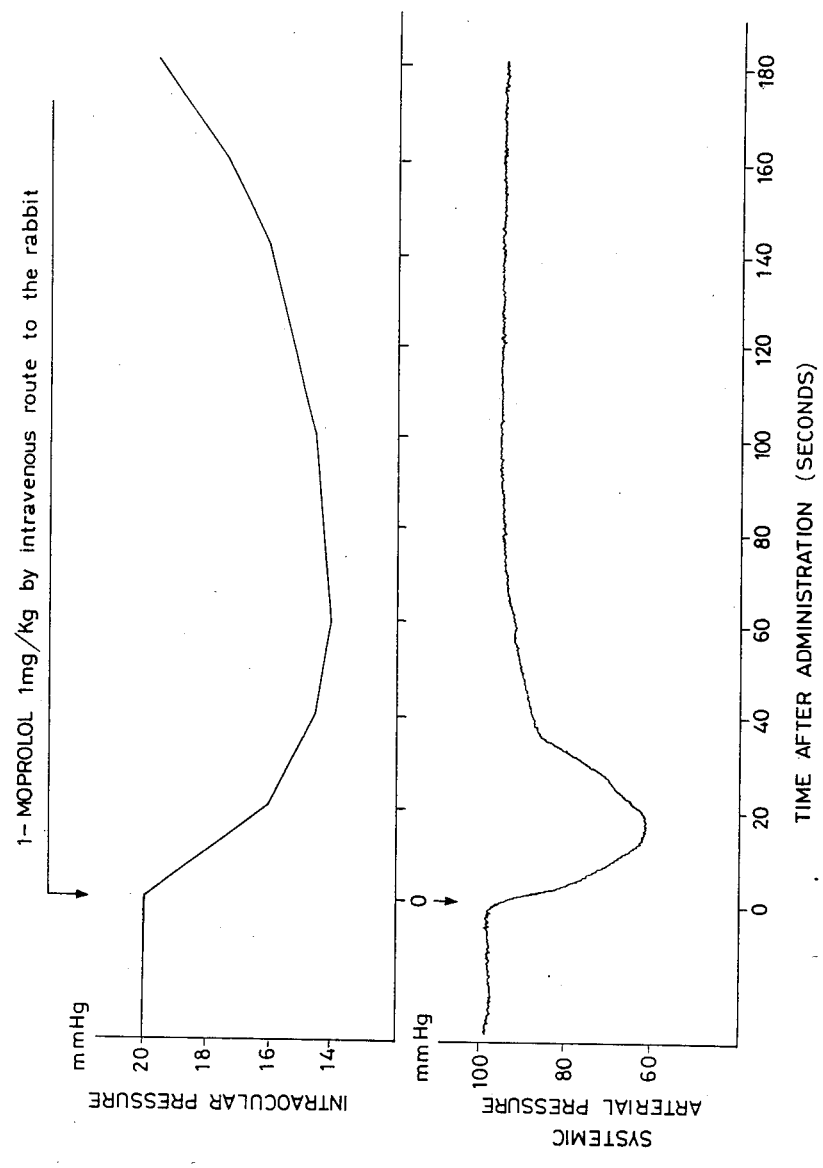
Figure 4:
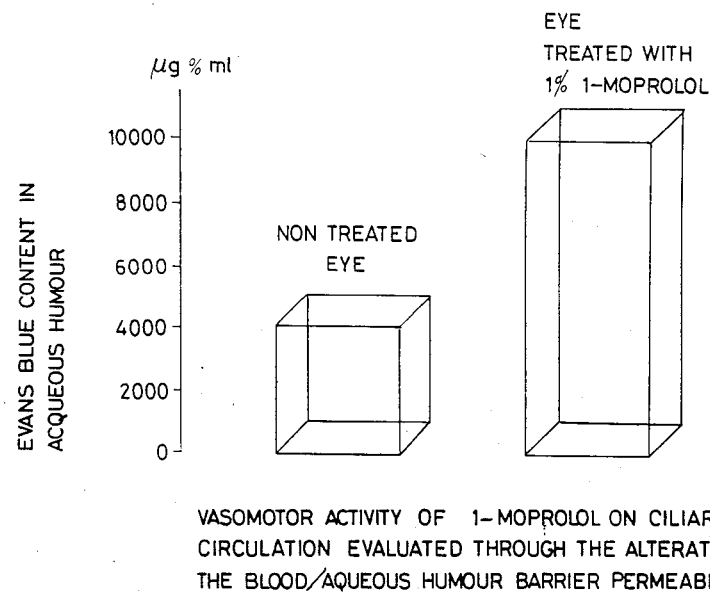
Figure 5:
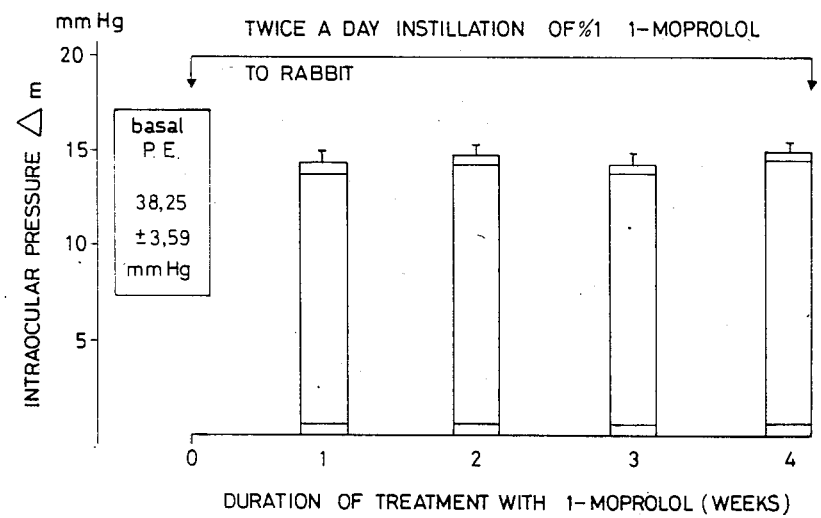

2. Solution
   1-moprolol (as hydrochloride salt): 0.500 g
   sodium chloride: 0.880
   benzalkonium chloride: 0.010
   monosodium phosphate monohydrate: 0.180
   disodium phosphate dihydrate: 0.220
   distilled water: q.s. to 100 ml 3. Solution
   1-moprolol (as hydrochloride salt): 4.00 g
   sodium chloride: 0.030 g
   benzalkonium chloride: 0.010 g
   monosodium phosphate monohydrate: 0.180 g
   disodium phosphate dihydrate: 0.220 g
   distilled water: q.s. to 100 ml 4. Ointment 1-moprolol (as hydrochloride salt): 1.00 g
   paraffin oil: 25.50 g White vaseline: 73.50 g The pharmacological activity of these collyria has been tested as follows:

experimental animal: rabbit;

measurement of intraocular pressure by an electronic tonometer (Mackay-Marg) after local anesthesia with 0.4% Novesine Wander;

experimentally induced hypertension: introduction in the anterior chamber of powder of Laminaria digitata (Priestley et al., Bollettino di Oculista, 47, (10), (1968), 652–668);

measurement of systemic arterial pressure: after isolation under local anesthesia with 1% Scurocaine, the femoral artery was cannulated by a polyvinyl catheter and the system connected with an electromanometer (Telco Thomson) and with a Varian C-2000 apparatus to record continously and graphically the arterial pressure;

measurement of vasomotor activity on the ciliary body by a technique based on the indirect evaluation of the ciliary permeability after paracentesis (Virno et al., Bolletino di Oculistica, 58, (1982), Supplemento al N. 11-12);

The results of the above mentioned tests have been the followings:

- l-moprolol exhibits a remarkable hypotensive effect either on the normal eye (FIG. 1) or, particularly, on the eye with experimentally induced ocular hypertension (FIG. 2);
- the biomicroscopic examination did not show significant alterations of cornea and conjunctiva neither after single instillation or after administration twice a day for 30 days;
- the instillation of the drug did not cause systemic effects;
- the intravenous administration caused a reduction of the intraocular pressure concomitant with the systemic hypotension, which means a passive partecipation of the intraocular circulation to the general vascular phenomenon (FIG. 3);
- the instillation of the compound under examination caused a response of the ciliary body which resulted in a vasodilation when was lacking the extracirculatory pressure whereas when this pressure was present the vasodilation phenomenon has been reversed in a "passive" vasocostriction with concomitant reduction of the vasal permeability and of the production of aqueous humour (Virno et al., Bollettino di oculistica, 58, (1982), Suppl. to No. 11-12) (FIG. 4);
- the tachyphylaxis evaluation showed that the amount of the intra-ocular hypotensive response is not reduced during the period of treatment (30 days) (FIG. 5)

Figure 6:
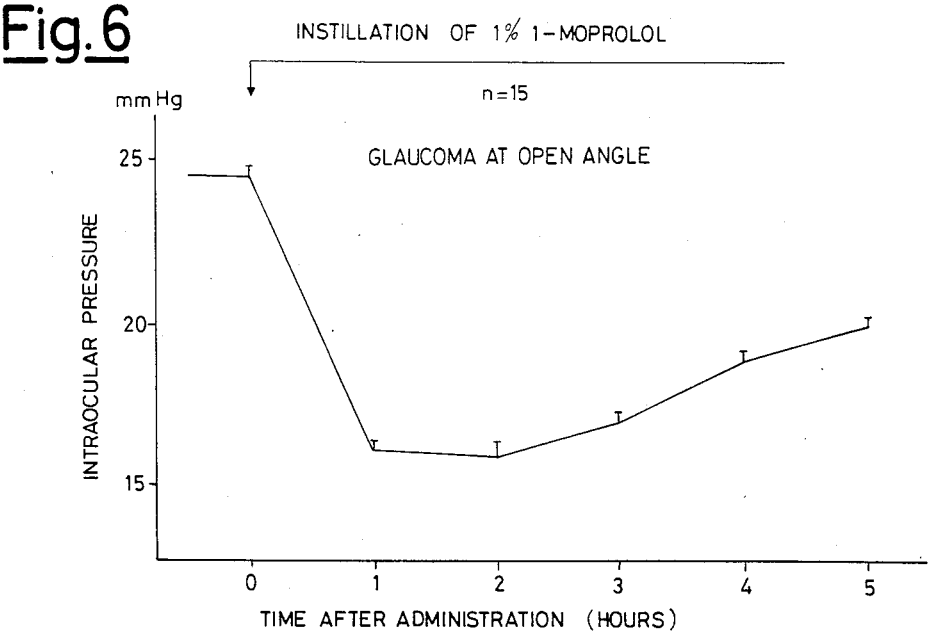
Figure 7:
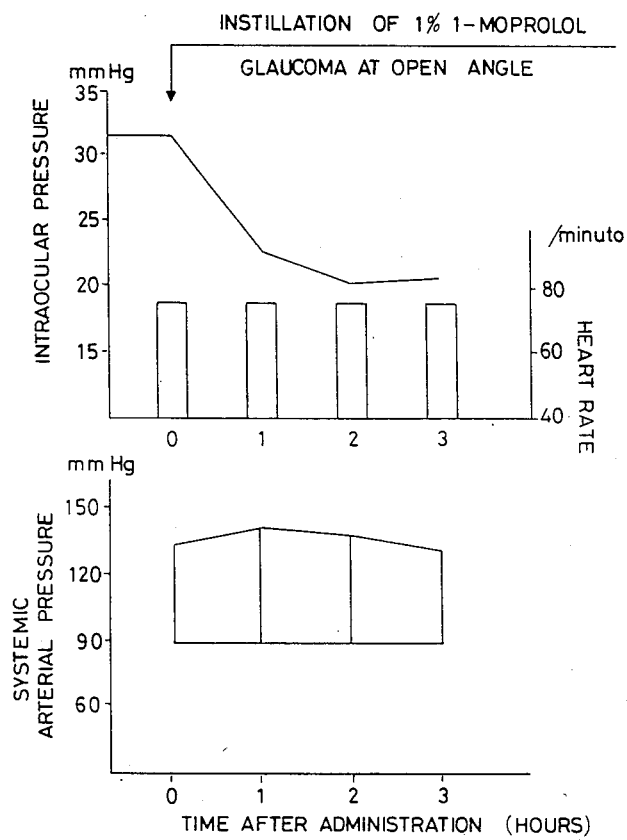

The above mentioned properties have been confirmed in humans; 20 patients suffering from simple cronic glaucoma have been treated 2-3 times a day with ½ drops (0.5/1 mg) of collyrium containing 1% l-moprolol. Treatment caused reduction of the intraocular pressure (FIG. 6) and the preparation resulted very well tolerated: no evidence of burnings or of side effects on the cornea. No heart rate or arterial pressure variation has been observed (FIG. 7).

I claim:

1. An opthalmic pharmaceutical composition for the treatment of glaucoma consisting essentially of form 0.1 to 20% by weight of l-moprolol or a pharmaceutically acceptable addition salt thereof together with a pharmaceutically acceptable fluid diluent.

2. An opthalmic pharmaceutical composition according to claim 1 containing from 1 to 8% by weight of l-moprolol.

3. A fluid opthalmic pharmaceutical composition for the treatment of glaucoma consisting essentially of 0.1 to 20% by weight of l-moprolol or a pharmaceutically acceptable salt thereof and a pharmaceutically acceptable fluid diluent, preservative, buffer or stabilizer.

4. The fluid opthalmic pharmaceutical composition according to claim 3 in the form of an opthalmic ointment.

5. The opthalmic ointment of claim 4 containing from 1 to 8% by weight of l-moprolol.

6. The fluid opthalmic pharmaceutical composition according to claim 3 in the form of an ophthalmic solution.

7. The ophthalmic solution of claim 6 containing from 1 to 8% by weight of l-moprolol.

8. A method of treating glaucoma comprising administering locally to a glaucoma patient from 0.5 to 6 mg. of l-moprolol per day.

9. The method according to claim 8 in which the l-moprolol is administered locally from 1 to 4 times a day.

10. A method of treating glaucoma in a subject having intraocular hypertension comprising installing in the eye of said subject an opthalmic pharmaceutical composition containing l-moprolol the amount of l-moprolol being in the range of 0.5 to 6 mg per day and sufficient to reduce the intraocular hypertension.

11. The method according to claim 10 in which the opthalmic pharmaceutical composition is administered from 1 to 4 times a day.

* * * * *